United States Patent
Mangual-Soto et al.

(10) Patent No.: US 11,564,606 B2
(45) Date of Patent: Jan. 31, 2023

(54) SYSTEM AND METHOD FOR ELECTROPHYSIOLOGICAL MAPPING

(71) Applicant: St. Jude Medical, Cardiology Division, Inc., St. Paul, MN (US)

(72) Inventors: Jan O. Mangual-Soto, Rho (IT); Louis-Philippe Richer, Montreal (CA); Chunlan Jiang, N. Crystal, MN (US); Cyrille Casset, Saint Selve (FR); Craig Markovitz, Leipzig (DE)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 408 days.

(21) Appl. No.: 16/623,219

(22) PCT Filed: Jul. 11, 2018

(86) PCT No.: PCT/US2018/041654
§ 371 (c)(1),
(2) Date: Dec. 16, 2019

(87) PCT Pub. No.: WO2019/018182
PCT Pub. Date: Jan. 24, 2019

(65) Prior Publication Data
US 2021/0145344 A1    May 20, 2021

Related U.S. Application Data

(60) Provisional application No. 62/534,550, filed on Jul. 19, 2017.

(51) Int. Cl.
*A61B 5/283*    (2021.01)
*G16H 50/30*    (2018.01)
(Continued)

(52) U.S. Cl.
CPC .............. *A61B 5/283* (2021.01); *A61B 5/061* (2013.01); *A61B 5/339* (2021.01); *A61B 5/6886* (2013.01);
(Continued)

(58) Field of Classification Search
None
See application file for complete search history.

(56) References Cited

U.S. PATENT DOCUMENTS 5,697,377 A    12/1997  Wittkampf
5,983,126 A    11/1999  Wittkampf
(Continued)

OTHER PUBLICATIONS

International Search Report and Written Opinion for PCT/US2018/041654, dated Oct. 22, 2018.

*Primary Examiner* — Ankit D Tejani
(74) *Attorney, Agent, or Firm* — Wiley Rein LLP

(57) ABSTRACT

The signal quality of an electrophysiological signal can be determined from information regarding proximal stability of an electrophysiology catheter at the time the signal is acquired and temporal stability of the electrophysiological signal. The proximal stability information can include a distance between the electrophysiology catheter and an anatomical surface, a velocity of the electrophysiology catheter, and/or contact force between the electrophysiology catheter and the anatomical surface. Graphical representations of signal quality scores can be output to a display in order to enable visualization thereof by a practitioner.

21 Claims, 4 Drawing Sheets

(51) Int. Cl.
*A61B 5/339* (2021.01)
*A61B 5/06* (2006.01)
*A61B 5/00* (2006.01)

(52) U.S. Cl.
CPC .......... *A61B 5/7221* (2013.01); *A61B 5/7264* (2013.01); *G16H 50/30* (2018.01)

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 2012/0184863 A1 | 7/2012 | Harlev et al. |
| 2014/0081114 A1 | 3/2014 | Shachar et al. |
| 2014/0180152 A1 | 6/2014 | Maskara et al. |
| 2015/0057507 A1 | 2/2015 | Koyrakh et al. |
| 2015/0228254 A1* | 8/2015 | Olson .................... G16Z 99/00 345/592 |

* cited by examiner

SYSTEM AND METHOD FOR ELECTROPHYSIOLOGICAL MAPPING

CROSS-REFERENCE TO RELATED APPLICATIONS

This application claims the benefit of U.S. provisional application No. 62/534,550, filed 19 Jul. 2017, which is hereby incorporated by reference as though fully set forth herein.

BACKGROUND

The present disclosure relates generally to electrophysiological mapping, such as may be performed in cardiac diagnostic and therapeutic procedures. In particular, the present disclosure relates to systems, apparatuses, and methods for quantifying electrophysiological signal quality (based on, e.g., tissue contact, contact stability, and/or signal stability).

Electrophysiological mapping, and more particularly electrocardiographic mapping, is a part of numerous cardiac diagnostic and therapeutic procedures. As the complexity of such procedures increases, however, the electrophysiology maps must increase in quality and in data density.

To increase the quality and density of electrophysiology maps, medical devices and systems (e.g., electrophysiology catheters, electroanatomical mapping systems) that simultaneously collect many (e.g., more than ten) intracardiac electrogram signals can be used. Extant devices and systems, however, often do not provide a practitioner with a quick, visual confirmation of the quality of the electrograms being collected.

BRIEF SUMMARY

Disclosed herein is a method of determining signal quality of an electrophysiological signal, including the steps of: receiving, at a signal processor information regarding proximal stability, relative to an anatomical region, of an electrophysiology catheter used to measure the electrophysiological signal at an acquisition time of the electrophysiological signal and information regarding temporal stability of the electrophysiological signal; and computing a signal quality score using the information regarding proximal stability and the information regarding temporal stability.

The information regarding proximal stability can include: information regarding a distance between the electrophysiology catheter and the anatomical surface at the acquisition time; and information regarding a velocity of the electrophysiology catheter at the acquisition time. It is also contemplated that the information regarding proximal stability can further include information regarding contact force between the electrophysiology catheter and the anatomical surface at the acquisition time.

According to aspects of the instant disclosure, the distance between the electrophysiology catheter and the anatomical surface can be measured using a geometric model of the anatomical region.

The method can also include outputting a graphical representation of the signal quality score. For example, a graphical representation of the electrophysiological signal can be colored to represent the signal quality score.

The steps of receiving, at a signal processor, information regarding proximal stability, relative to an anatomical region, of an electrophysiology catheter used to measure the electrophysiological signal at an acquisition time of the electrophysiological signal and information regarding temporal stability of the electrophysiological signal; and computing a signal quality score using the information regarding proximal stability and the information regarding temporal stability can be repeated for a plurality of electrophysiological signals to create a signal quality map. In turn, it is contemplated that a graphical representation of the signal quality map can be output. For example, the graphical representation of the signal quality map can be output on a geometric model of the anatomical region.

Also disclosed herein is a method of mapping electrophysiological signal quality, including: receiving an electrophysiological signal; and computing a signal quality score for the received electrophysiological signal as a function of two or more of a surface proximity parameter, a contact force parameter, and a signal temporal stability parameter.

In embodiments, the method further includes outputting a graphical representation of the computed signal quality score. For example, a graphical representation of the electrophysiological signal can be colored according to the computed signal quality score.

Aspects of the disclosure relate to repeating the step of computing a signal quality score for the received electrophysiological signal as a function of two or more of a surface proximity parameter, a contact force parameter, and a signal temporal stability parameter for a plurality of received electrophysiological signals, to create a signal quality map. In turn, the method can further include outputting a graphical representation of the signal quality map, for example on a geometric model of an anatomical region from which the plurality of received electrophysiological signals originated.

The surface proximity parameter can be based at least in part upon a distance from an electrophysiology catheter receiving the received electrophysiological signal and an anatomical region from which the received electrophysiological signal originated at an acquisition time of the received electrophysiological signal. The surface proximity parameter can additionally or alternatively be based at least in part upon a velocity of the electrophysiology catheter at the acquisition time.

In embodiments, the function is a function of all of the surface proximity parameter, the contact force parameter, and the signal temporal stability parameter. For example, the function can be of form $QS=TS*[CF+(1-CF)*PS]$, where QS is the signal quality score; TS is the signal temporal stability parameter; CF is the contact force parameter; and PS is the surface proximity parameter.

The instant disclosure also provides a system for determining signal quality of an electrophysiological signal measured at an acquisition time from an anatomical region using electrophysiology catheter. The system includes: a signal quality processor configured to: receive as input information regarding proximal stability of the electrophysiology catheter relative to the anatomical region at the acquisition time; receive as input information regarding temporal stability of the electrophysiological signal; and compute a signal quality score using the information regarding proximal stability and the information regarding temporal stability.

According to aspects of the disclosure, the information regarding proximal stability includes: information regarding a distance between the electrophysiology catheter and the anatomical surface at the acquisition time; and information regarding a velocity of the electrophysiology catheter at the acquisition time. The information regarding proximal stability can also include information regarding contact force between the electrophysiology catheter and the anatomical surface at the acquisition time.

It is also contemplated that the system can include a mapping processor configured to output a graphical representation of the signal quality score.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for determining electrophysiological signal quality. For purposes of illustration, aspects of the disclosure will be described in connection with a cardiac electrophysiological study. It should be understood, however, that the teachings herein can be applied to good advantage in other contexts.

Figure 1:
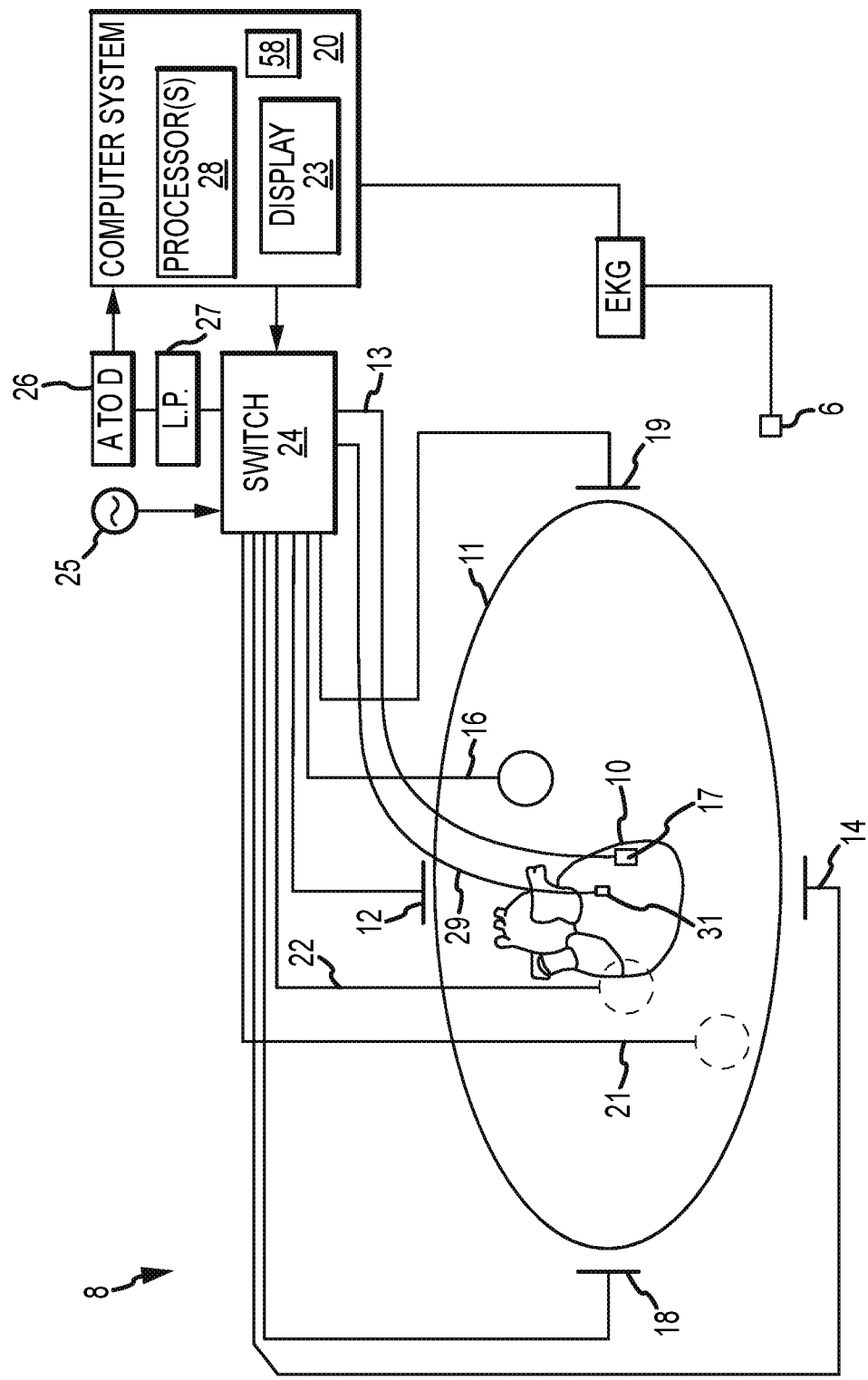
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10. In some embodiments, and as discussed further herein, the system 8 can determine the signal quality of measured electrophysiological data and compute a corresponding signal quality score.

As one of ordinary skill in the art will recognize, and as will be further described below, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. Of course, this embodiment is merely exemplary, and any number of electrodes and catheters may be used.

Figure 2:
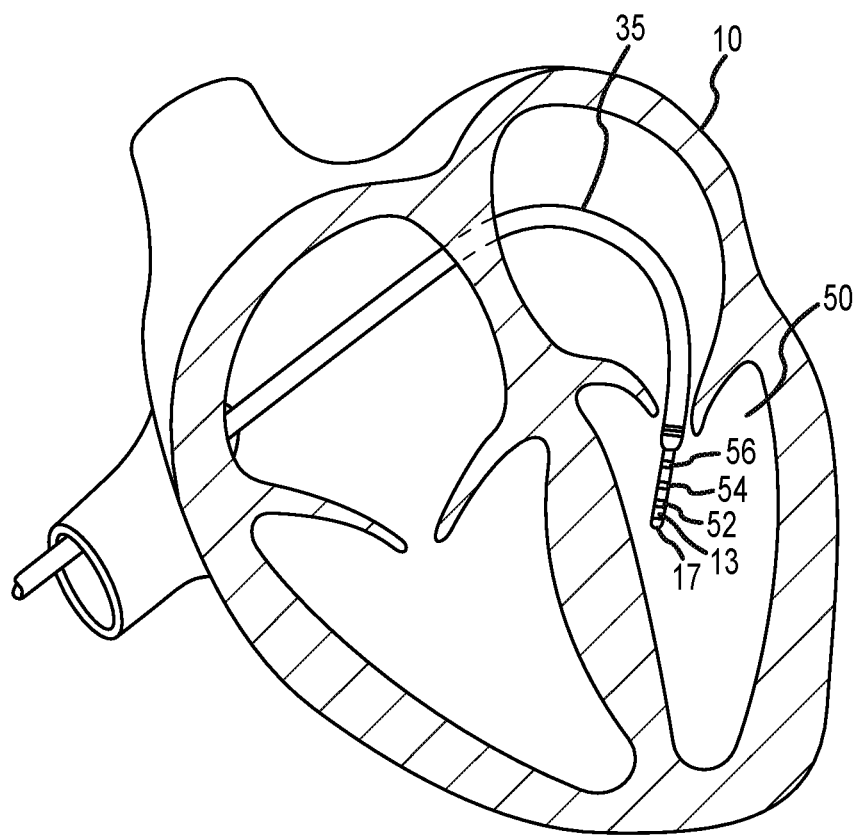
FIG. 2 depicts an exemplary catheter that can be used in connection with aspects of the instant disclosure.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner (e.g., via epicardial access).

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the instant disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ or EnSite Precision™ cardiac mapping and visualization system of Abbott Laboratories. Other localization systems, however, may be used in connection with the present teachings, including for example the CARTO navigation and location system of Biosense Webster, Inc., the AURORA® system of Northern Digital Inc., Sterotaxis' NIOBE® Magnetic Navigation System, as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to computing signal quality scores (e.g., indices of the quality of the electrophysiology signals collected by electrodes 17, 52, 54, 56). System 8 can therefore also include a signal quality module 58 (e.g., executing on processor 28) that can be used to determine signal quality scores.

Figure 3:
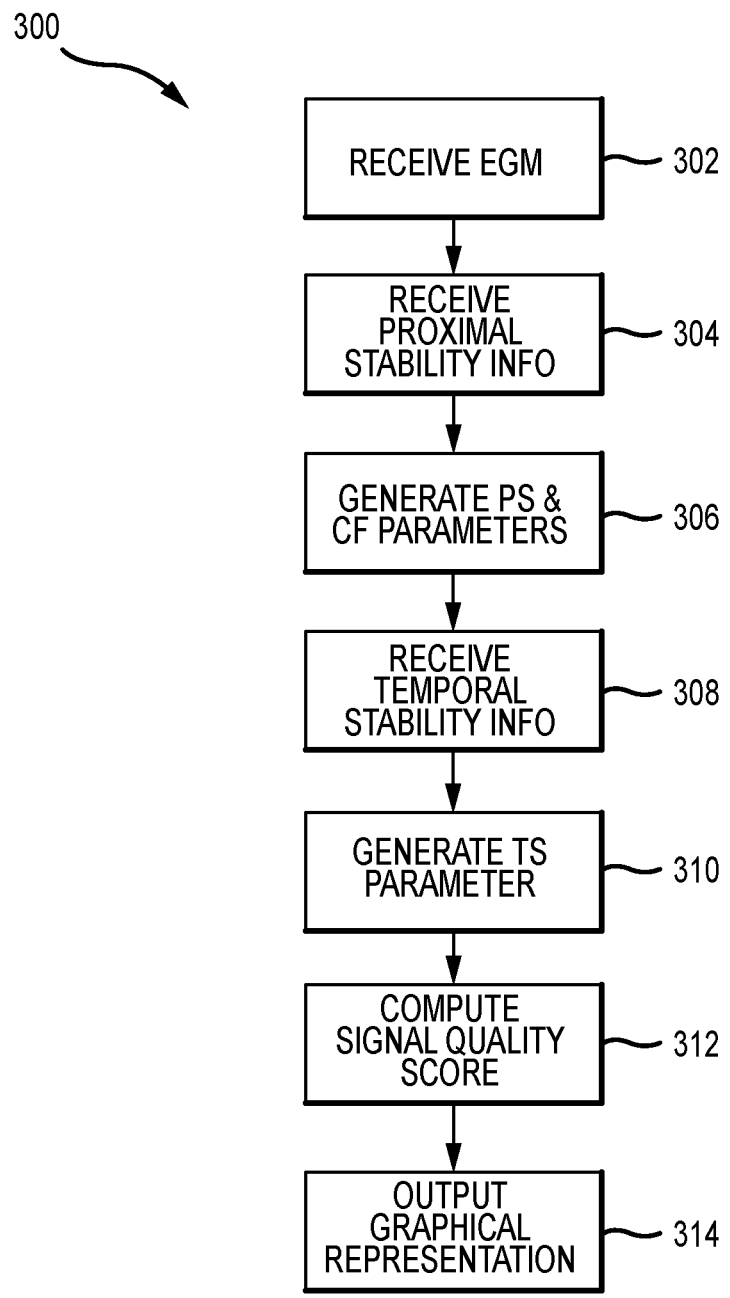
FIG. 3 is a flowchart of representative steps that can be followed according to exemplary embodiments disclosed herein.

One exemplary method of determining signal quality indices according to the present teachings will be explained with reference to the flowchart 300 of representative steps shown in FIG. 3. In some embodiments, for example, flowchart 300 may represent several exemplary steps that can be carried out by electroanatomical mapping system 8 of FIG. 1 (e.g., by processor 28 and/or signal quality module 58). It should be understood that the representative steps described below can be either hardware- or software-implemented. For the sake of explanation, the term "signal processor" is used herein to describe both hardware- and software-based implementations of the teachings herein.

It should also be understood that the representative steps described below can be carried out in real time (e.g., upon an intracardiac electrogram at the time of collection during an electrophysiology study) or as post-processing (e.g., upon an intracardiac electrogram that was collected during an electrophysiology study performed at an earlier time). That is, the electrogram signal received in block 302 of FIG. 3 can be a real-time electrogram signal or an electrogram signal that is part of a data set undergoing post processing.

In block 304, the signal processor receives information regarding the proximal stability of an electrophysiology catheter (e.g., catheter 13) used to measure the electrogram signal received in block 302 at the time that signal was acquired. The proximal stability information is determined relative to an anatomical region, such as the cardiac surface being studied.

For example, the proximal stability information can include a distance between catheter 13 and the cardiac surface at the signal acquisition time. In some aspects of the disclosure, the distance between catheter 13 and the cardiac surface is measured using a geometric model of the anatomical region (e.g., a cardiac geometry generated by electroanatomical mapping system 8, but it is also regarded as within the scope of the instant disclosure to measure the distance in other ways (e.g., ultrasound, fluoroscopy).

As another example, in additional embodiments of the disclosure, the proximal stability information can also include information regarding contact force between catheter 13 and the cardiac surface at the signal acquisition time.

The proximal stability information can also include information regarding the velocity of catheter 13 at the signal acquisition time.

In block 306, the proximal stability information is used to generate a surface proximity signal quality parameter ("PS") and a contact force signal quality parameter ("CF"). For example, PS can be defined as follows:

$$PS = \begin{cases} 1, & \text{if } d < 5 \text{ mm AND } v < 10 \text{ mm/sec} \\ 0, & \text{otherwise} \end{cases}$$

where d is the distance between catheter 13 and the cardiac surface at the signal acquisition time and v is the velocity of catheter 13 at the signal acquisition time. Other definitions of PS, including non-linear functions, are also contemplated as within the scope of the instant disclosure.

Likewise, CF can be defined as follows:

$$CF = \begin{cases} 1, & \text{if } F > 2g \\ 0, & \text{otherwise} \end{cases}$$

where F is the contact force between catheter 13 and the cardiac surface. Those of ordinary skill in the art will understand that, according to the foregoing equation, CF will also be set to 0 if catheter 13 lacks a contact force sensor. Other definitions of CF, including non-linear functions, are also contemplated as within the scope of the instant disclosure.

In block 308, the signal processor receives information regarding the temporal stability of the electrogram signal received in block 302. Then, in block 310, the temporal stability information is used to generate a temporal stability signal quality parameter ("TS").

Figure 4:
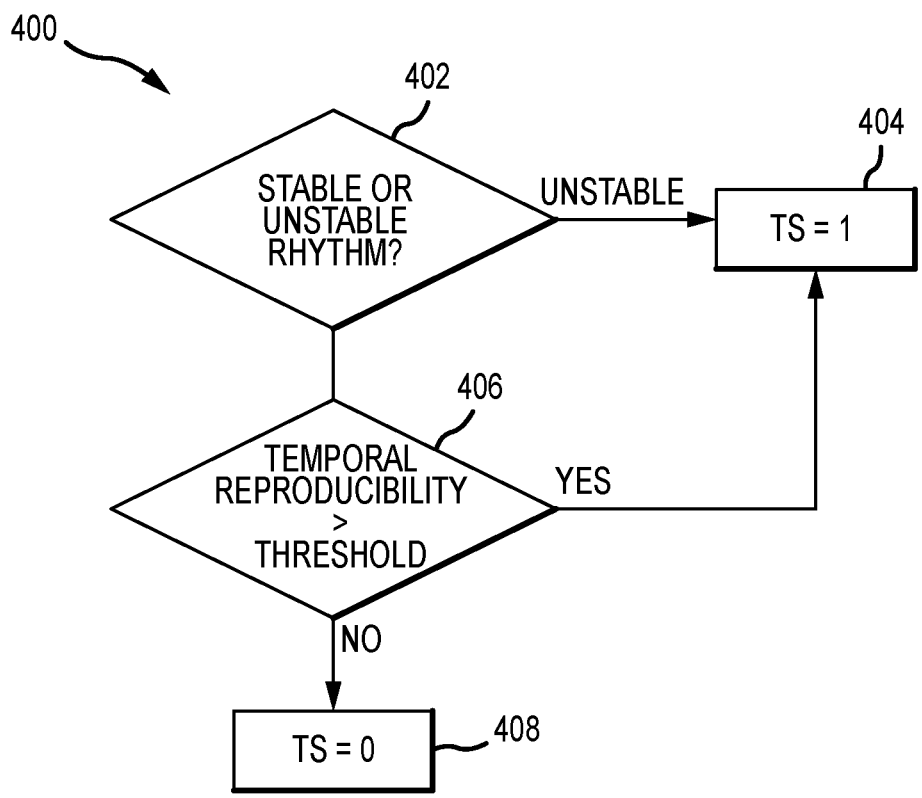
FIG. 4 depicts a flowchart of representative steps that can be used to compute a signal temporal stability signal quality parameter.

One approach to generating TS will be described with reference to the flowchart 400 of FIG. 4. Decision block 402 determines whether the received electrogram signal is part of a stable rhythm (e.g., sinus rhythm; stable tachycardia) or an unstable rhythm. For an unstable rhythm, TS=1 (block 404).

For a stable rhythm, decision block 406 determines whether the signal has a temporal reproducibility above a reproducibility threshold (e.g., 80%). If not, TS=0 (block 408). If so, TS=1 (block 404). This reduces the likelihood that ectopic beats and/or noise signal artifacts will be acquired.

Once the signal quality parameters are generated, they can be used to compute a signal quality score for the received electrogram in block 312. For example, a quality score ("QS") can be computed according to the equation QS=TS*[CF+(1−CF)*PS].

In block 314, a graphical representation of the signal quality score can be output (e.g., to display 23). For example, a visual trace of the received electrogram signal can be displayed in a color, or using a color scale, that corresponds to the computed quality score (e.g., high quality signals (e.g., quality scores greater than or equal to about 90) can be colored white, while low quality signals (e.g., quality scores less than or equal to about 80) can be colored red). It is contemplated that the thresholds for high and low quality scores can be user-defined and/or user-adjustable.

As another example, the numerical quality score can be shown on display 23 adjacent the corresponding visual trace of the received electrogram. To enhance the visibility of the quality score, progressively larger fonts can be used to display the numerical quality score as the quality score increases. Analogous font scaling can also be applied to other displayed text associated with the received electrogram (e.g., a lead designator) in addition to or as an alternative to the displayed numerical quality score.

The teachings above, which are described with reference to a single electrogram, can be applied to multiple electrograms, thereby creating a signal quality map. The signal quality map can also be output as a graphical representation in a manner analogous to other electrophysiology maps, which techniques will be familiar to those of ordinary skill in the art. For example, United States patent application publication no. 2015/0228254, which is hereby incorporated by reference as though fully set forth herein, discloses, among other things, the use of glyphs to graphically represent biological attributes. In embodiments of the disclosure, one or more glyph attributes (e.g., color, size, transparency, or the like) can be used to display signal quality.

By providing the practitioner with a visual indication of signal quality, the practitioner will be able to ascertain, in real time, whether a particular electrophysiology data point should be stored and/or if catheter 13 should be repositioned prior to storing an electrophysiology data point. The techniques described herein can also be used to remove undesirable electrophysiology data points (e.g., ectopic beats; noise artifacts) from an electrophysiology map in post-processing, thereby improving the quality of the electrophysiology map.

Although several embodiments have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of determining signal quality of an electrophysiological signal, comprising:
   receiving, at a signal processor:
      information regarding proximal stability, relative to an anatomical region, of an electrophysiology catheter used to measure the electrophysiological signal at an acquisition time of the electrophysiological signal; and
      information regarding temporal stability of the electrophysiological signal;
   computing a signal quality score using the information regarding proximal stability and the information regarding temporal stability,
   wherein the signal quality score comprises a numerical score computed according to a function of form $QS=TS*[CF+(1-CF)*PS]$, where QS is the signal quality score; TS is a signal temporal stability parameter reflecting the information regarding temporal stability; CF is a contact force parameter; and PS is a surface proximity parameter.

2. The method according to claim 1, wherein the information regarding proximal stability comprises:
   information regarding a distance between the electrophysiology catheter and an anatomical surface at the acquisition time; and
   information regarding a velocity of the electrophysiology catheter at the acquisition time.

3. The method according to claim 2, wherein the distance between the electrophysiology catheter and the anatomical surface is measured using a geometric model of the anatomical region.

4. The method according to claim 1, wherein the information regarding proximal stability further comprises information regarding contact force between the electrophysiology catheter and an anatomical surface at the acquisition time.

5. The method according to claim 1, further comprising repeating:
   receiving, at a signal processor:
      information regarding proximal stability, relative to an anatomical region, of an electrophysiology catheter used to measure the electrophysiological signal at an acquisition time of the electrophysiological signal; and
      information regarding temporal stability of the electrophysiological signal; and
   computing a signal quality score using the information regarding proximal stability and the information regarding temporal stability for a plurality of electrophysiological signals to create a signal quality map.

6. The method according to claim 5, further comprising outputting a graphical representation of the signal quality map.

7. The method according to claim 6, wherein outputting a graphical representation of the signal quality map comprises outputting the graphical representation of the signal quality map on a geometric model of the anatomical region.

8. The method according to claim 1, further comprising outputting a graphical representation of the signal quality score.

9. The method according to claim 8, wherein outputting the graphical representation of the signal quality score comprises coloring a graphical representation of the electrophysiological signal.

10. A method of mapping electrophysiological signal quality, comprising:
    receiving an electrophysiological signal;
    computing a signal quality score for the received electrophysiological signal as a function of two or more of a surface proximity parameter, a contact force parameter, and a signal temporal stability parameter, wherein the function is of form $QS=TS*[CF+(1-CF)*PS]$, where QS is the signal quality score; TS is the signal temporal stability parameter; CF is the contact force parameter; and PS is the surface proximity parameter.

11. The method according to claim 10, further comprising repeating the step of computing a signal quality score for the received electrophysiological signal as a function of two or more of a surface proximity parameter, a contact force parameter, and a signal temporal stability parameter for a plurality of received electrophysiological signals, to create a signal quality map.

12. The method according to claim 11, further comprising outputting a graphical representation of the signal quality map.

13. The method according to claim 12, wherein outputting a graphical representation of the signal quality map comprises outputting a graphical representation of the signal quality map on a geometric model of an anatomical region from which the plurality of received electrophysiological signals originated.

14. The method according to claim 10, wherein the surface proximity parameter is based at least in part upon a distance from an electrophysiology catheter receiving the received electrophysiological signal and an anatomical region from which the received electrophysiological signal originated at an acquisition time of the received electrophysiological signal.

15. The method according to claim 14, wherein the surface proximity parameter is based at least in part upon a velocity of the electrophysiology catheter at the acquisition time.

16. The method according to claim 10, further comprising outputting a graphical representation of the computed signal quality score.

17. The method according to claim 16, wherein outputting the graphical representation of the computed signal quality score comprises coloring a graphical representation of the electrophysiological signal.

18. A system for determining signal quality of an electrophysiological signal measured at an acquisition time from an anatomical region using an electrophysiology catheter, the system comprising:
a signal quality processor configured to:
receive as input information regarding proximal stability of the electrophysiology catheter relative to the anatomical region at the acquisition time;
receive as input information regarding temporal stability of the electrophysiological signal; and
compute a signal quality score using the information regarding proximal stability and the information regarding temporal stability, wherein the signal quality score comprises a numerical score computed according to a function of form QS=TS*[CF+(1−CF)*PS], where QS is the signal quality score; TS is a signal temporal stability parameter reflecting the information regarding temporal stability; CF is a contact force parameter; and PS is a surface proximity parameter.

19. The system according to claim 18, wherein the information regarding proximal stability comprises:
information regarding a distance between the electrophysiology catheter and an anatomical surface at the acquisition time; and
information regarding a velocity of the electrophysiology catheter at the acquisition time.

20. The system according to claim 18, wherein the information regarding proximal stability comprises information regarding contact force between the electrophysiology catheter and an anatomical surface at the acquisition time.

21. The system according to claim 18, further comprising a mapping processor configured to output a graphical representation of the signal quality score.

* * * * *